United States Patent [19]

Gomez et al.

[11] 4,224,406
[45] Sep. 23, 1980

[54] IMMUNOCHEMICAL LDH$_1$ ASSAY

[75] Inventors: Magdalena U. Gomez, Wayne; Richard W. Wicks, Belleville, both of N.J.

[73] Assignee: Hoffmann-La Roche Inc., Nutley, N.J.

[21] Appl. No.: 882,013

[22] Filed: Feb. 27, 1978

[51] Int. Cl.$^3$ .................. C12Q 1/66; C12Q 1/32
[52] U.S. Cl. .................................. 435/7; 424/12; 435/26
[58] Field of Search ............... 195/103.5 A, 103.5 R; 424/212; 23/230 B; 435/7, 26

[56] References Cited

U.S. PATENT DOCUMENTS

| | | | |
|---|---|---|---|
| 3,932,221 | 1/1976 | Pfleiderer | 195/103.5 R |
| 4,012,285 | 3/1977 | Pfleiderer et al. | 195/103.5 A |
| 4,046,634 | 9/1977 | Mercer | 195/103.5 R |
| 4,048,298 | 9/1977 | Niswender | 23/230 B X |

FOREIGN PATENT DOCUMENTS 2128670 12/1972 Fed. Rep. of Germany ... 195/103.5 A
2350711 4/1975 Fed. Rep. of Germany .

OTHER PUBLICATIONS

Murket, et al., "Immunochemical Properties of Lactate Dehydrogenase Isoenzymes", *Ann. N.Y. Acad. Sci.*, vol. 103 (1963), pp. 915-929.
Sussmann, et al., "Human Alkaline Phosphatase", *J. Biol. Chem.*, vol. 243, No. 1 (1968), pp. 160-166.
Boll, et al., "Quantitative Immunological Determination of Multiple Forms of the Lactate Dehydrogenase in Animal and Human Tissue", *Hoppe-Seyler's Z. Physiol. Chem.*, vol. J55 (1974), pp. 811-818.
Clark, et al., "A Simple and Rapid Procedure for the Preparation of Human LDH-1 and LDH-5 Using an Ion-Exchange-Column", *Chem. Abst.*, vol. 85, No. 7 (1976), p. 217, abs. #42732a.

*Primary Examiner*—Thomas G. Wiseman
*Attorney, Agent, or Firm*—Jon S. Saxe; George M. Gould

[57] ABSTRACT

LDH$_1$ levels in serum samples can be rapidly and accurately assayed by a novel immunochemical technique. In such procedure the serum sample is treated with soluble antibodies against the M subunit and the resulting antigen-antibody reaction product is insolubilized with a second antibody supported on an insoluble material. The resulting supernatant containing only LDH, isoenzyme is assayed for enzymatic activity by conventional procedures. The assay of LDH$_1$ levels in sera is useful in determining whether the subject has undergone a myocardial infarction.

5 Claims, No Drawings

IMMUNOCHEMICAL $LDH_1$ ASSAY

BACKGROUND OF THE INVENTION

U.S. Pat. No. 4,046,634 discloses an assay for isoenzymes, including LDH isoenzymes, which employs ion exchange column chromatography to isolate a mixture of $LDH_1$ and $LDH_2$ isoenzymes which are then detected by conventional techniques such as the Wacker LDH method.

German Auslegeschrift No. 21 28 670 discloses a method for assaying for isoenzymes, including LDH isoenzymes by treating the test sample with a large excess of a specific antibody to either $LDH_1$ or $LDH_5$ isoenzymes so as to effect quantitative precipitation of the antigen-antibody complex. After incubation and centrifugation of the precipitated complex, the enzyme activity of the supernatant was determined by the method reported in Z. Klin. Chemie und Klin. Biochemie 8, 658 (1970).

Sussman et al., Journal of Biological Chemistry 243, 160 (1968) have described an assay for individual organ specific isoenzymes of human alkaline phosphate using a two step procedure. In the first step the specific antibody to the desired isoenzyme was reacted with the test sample and then in a subsequent step the antibody-antigen complex is precipitated with a second antibody (anti-$\gamma$-globulin). After centrifugation the supernatant is tested for residual isoenzyme activity.

The use of a second antibody insolubilized on a solid support material in radioimmunoassay procedures is described in U.S. Pat. No. 4,048,298. The disclosure includes the use of second antibodies adsorbed to the surface of polymeric solid support materials.

U.S. Pat. No. 3,843,443 relates to a method of immobilizing proteins on a fluorocarbon polymer support. Included within the disclosed proteins are antibodies and the preferred polymer support material is polyvinylidene fluoride (Kynar-a trademark of the Pennwalt Corp.).

DESCRIPTION OF THE INVENTION

The present invention relates to an improved immunochemical assay for the isoenzyme $LDH_1$ which isoenzyme is a known marker for myocardial infarction.

In the improved method of the present invention a test sample such as a serum sample, is treated with a soluble antibody specific against the M subunit of the LDH isoenzymes, i.e., $LDH_2$, $LDH_3$, $LDH_4$ and $LDH_5$. After mixing and incubating for a short time, a second antibody insolubilized on a solid phase support material is added and the mixture is mixed and then incubated for another short period. The insoluble antigen-antibody(1)-antibody(2)-solid support complex is centrifuged down and the supernatant tested for LDH enzyme activity. The activity observed will be essentially that of the $LDH_1$ isoenzyme component of the original sample.

The method of the present invention has substantial advantages over procedures utilized in the prior art for isoenzyme assay. It is very rapid, highly accurate and reproducible. The preparation of the $LDH_1$ containing supernatant can be accomplished in a matter of minutes instead of the substantial number of hours previously required for immunological techniques. Moreover, the present method provides a clean separation of $LDH_1$ from the other LDH isoenzymes which is not possible by ionexchange column procedures.

The specific antibody against the M subunit of LDH used in the present invention is known in the art. See for example the previously indicated German Auslegeschrift No. 21 28 670. Further disclosures relating to such antibody are to be found in J. S. Burd et al., Clinica Chimica Acta 46, 205-216 (1973) and J. S. Burd et al., Biochimica, Biophysica Acta, 310, 238-247 (1973).

The second antibody is prepared by immunization of a different animal than the one in which the specific first antibody is prepared with a gamma globulin from the blood of the host species used for the first antibody preparation. Thus the second antibody will be immunoreactive for the first antibody and will complex with it.

The second antibody is insolubilized by attaching said second antibody to an insoluble support material. Suitable support materials include water insoluble organic polymeric substances such as cellulose or other polysaccharide, a vinyl addition polymer or condensation polymer or a water insoluble inorganic substance of polymeric nature, such as glass or silicone resins or the second antibody may be adsorbed to the surface of a solid support such as polystyrene, polypropylene, polyfluoroethylene or polyvinylidene fluoride. The method of attachment of the second antibody to the solid support is not narrowly critical and may include (1) covalently coupling the soluble second antibody to any insoluble polymeric substance; (2) converting the soluble second antibody to an insoluble polymerized form, such as by reaction with an insolubilizing agent; (3) physical entrapment of particles of the second antibody in the pores of a gel polymer such as a cross-linked polyacrylamide; or (4) by physical adsorption on an insoluble polymeric substance.

In a preferred embodiment of the present invention the second antibody is supported by adsorption on activated Kynar utilizing the general procedures disclosed in U.S. Pat. No. 3,843,443.

The method of the present invention is further illustrated by reference to the following Example.

Example

1. Reagents a. Antiserum to $LDH_5$: goat anti $LDH_5$ serum is diluted to a concentration that binds 300–400 IU/l of purified $LDH_5$ isoenzyme employing Fisher Diagnostic or equivalent reagents for the determination of LDH enzymatic activity. The dilution of the antiserum is made in 0.02M Tris pH 7.5 with 0.1% $NaN_3$.

b. Insoluble antiserum to goat gamma globulin.

The following specific steps are followed in preparing an insoluble antiserum to goat gamma globulin (second antibody). The starting material is unsintered Kynar (vinylidene fluoride) resin powder, grade 301 F, Pennwalt Corp. The powder is dispersed in isopropanol (2-propanol) in the proportions of 50 grams Kynar in 1000 ml of isopropanol. The suspension is then homogenized by a Brinkmann Polytron for 5 minutes at a pulse-frequency of 4000 c.p.s. The Kynar-isopropanol mixture is then transferred to a cylinder containing ten liters of saline and stirred until dispersed. The Kynar is then allowed to settle out and most of the supernatant is decanted. After two water washes, the Kynar is resuspended in phosphate buffered saline (pH 7.0) with merthiolate (0.01%) to yield a 2% Kynar concentration. The Kynar is now in the activated state and able to accept protein. While the isopropanol activated Kynar is stirring, 0.5 ml of donkey antigoat gamma globulin serum per gram of Kynar is added. The mixture is then homogenized again by the Polytron for 5 minutes at the same pulse-frequency as before. The suspension is then continuously stirred at room temperature for a minimum of 6 hours followed by stirring at 4° C. for a minimum of 12 hours. The suspension is now ready to be washed. This is accomplished by centrifugation at 1500×g for 10 minutes followed by resuspension in 0.02M Tris Hydroxymethylaminomethane (Tham) pH 7.5 with 0.1% $NaN_3$. This process is repeated once more and the final material resuspended in 0.02M Tris pH 7.5 with 0.1% $NaN_3$ to 100 grams of Kynar per 1000 ml of buffer. The mixture is again stirred and 5 grams of bovine serum albumin (BSA) per 100 grams of Kynar added. Homogenization with the Polytron at 4000 c.p.s. for 5 minutes is the final step in this procedure.

2. Procedure a. To 200 μl of patient's serum add 10 μl of soluble goat anti $LDH_5$ serum and vortex. Wait 5 minutes.

b. Add 200 μl of insoluble second antibody* and vortex. Wait 5 minutes.

*Make sure that the insoluble antibody suspension is mixed well before use. Place a small stirring bar in the reagent bottle and keep mixing while delivering the antibody.

c. Spin at approximately 1000 g for 5 minutes.

d. Withdraw from the supernatant whatever amount is needed for a conventional LDH activity assay. Use same assay procedure.

3. Calculations $LDH_1$ activity = Activity in supernatant × 2.05

4. Interpretation

To decide on a cut-off point for $LDH_1$ an arbitrary value is established. This value will differ for each individual laboratory depending on the normal total LDH range of the enzyme assay being used. To establish an upper limit of normal for $LDH_1$ ($H_4$) take 30% of the upper level of normal for the total LDH enzyme activity assay. For example, the Fisher Diagnostic LDH Assay provided an upper limit of normal of 149 I.U./l. (The normal range is 52–149 I.U./l.) Therefore, the cut-off point adopted turned out to be 30% of 149 or 45 I.U./l. Any serum showing an $LDH_1$ activity above 45 I.U./l will be considered positive for myocardial infarct.

Clinical Results

Sera from 106 patients from a Cardiac Care Unit were examined for $LDH_1$ elevation. In all 72 patients where a myocardial infarct was diagnosed, an $LDH_1$ elevation was observed. However, $LDH_1$ remained non-elevated for all 34 non-myocardial infarct patients. A cutoff of 45 IU/l was designated for biochemical diagnoses of infarct. The range for $LDH_1$ activity in MI patients was 46–470 IU/l. The range for the non-MI patients was 9–44 IU/l. Presently most laboratories determine the $LDH_1/LDH_2$ "flip" by electrophoresis. This technique is tedious and time consuming. By contrast the present immunochemical procedure is simple and fast. In addition, determining $LDH_1$ elevation is more sensitive than the flip. In 59 of the 72 MI patients, the LDH flip occurred the same day as the $LDH_1$ evaluation. However, in 8 cases the LDH flip occurred one day after the $LDH_1$ elevation, and in 5 MI patients a flip was not obtained (see Tables I, II and III).

TABLE I

| Number of MI patients | LDH-1 Elevated | LDH Flip | | |
| --- | --- | --- | --- | --- |
| | | Same day as LDH-1 elevation | Day after LDH-1 elevation | Not present |
| 72 | 72 | 59 | 8 | 5 |

TABLE II

| Number of Non-MI patients | LDH-1 Elevated | LDH-Flip Present |
| --- | --- | --- |
| 34 | None | None |

TABLE III

Part A

| Number of MI patients | CPK-MB Present | LDH-1 Elevated | | | LDH Flip Present | | |
| --- | --- | --- | --- | --- | --- | --- | --- |
| | | Same Day as CPK | One Day after CPK | Not at All | Same Day as CPK | One Day after CPK | Not at All |
| 58 | 55 | 43 | 12 | None | 31 | 19 | 5 |

Part B

| Number of MI patients | DPK-MB Absent | LDH-1 Elevated | LDH Flip Present | | |
| --- | --- | --- | --- | --- | --- |
| | | | Same Day as LDH-1 Elevation | One Day after LDH-1 Elevation | Not at All |
| 58 | 3 | 3 | 2 | 1 | None |

What is claimed is:

1. An improved method for assaying $LDH_1$ activity in a serum sample which method comprises the following steps in combination:
   (A) mixing and incubating said serum sample with a first antibody immunologically selective for the M subunit of LDH isoenzymes for a short period of time sufficient to forms antibody complexes with $LDH_2$, $LDH_3$, $LDH_4$ and $LDH_5$ present in said sample;
   (B) mixing and incubating the immunological reaction product of step (A) with a second antibody immunogenically produced in an animal species other than the animal species used in producing said first antibody, said second antibody being insolubilized on a solid phase support material, for a short period of time sufficient to form an immunological reaction product between the product of step A and said insolubilized second antibody;
   (C) separating said reaction product of step (B) from the supernatant solution; and
   (D) assaying the supernatant solution for $LDH_1$ activity.

2. The method of claim 1 wherein said second antibody is insolubilized on activated polyvinylidene fluoride.

3. The method of claim 2 wherein said first antibody is goat anti-$LDH_5$ antibody.

4. The method of claim 3 wherein said second antibody is donkey anti-goat gamma globulin.

5. The method of claim 1 wherein the reaction mixture of step (A) is mixed and incubated for about five minutes before proceeding to step (B).

* * * * *